United States Patent [19]

Baldwin

[11] Patent Number: 5,162,733
[45] Date of Patent: Nov. 10, 1992

[54] METHOD FOR DETERMINING RELATIVE WETTABILITY

[75] Inventor: Bernard A. Baldwin, Bartlesville, Okla.

[73] Assignee: Philllips Petroleum Company, Bartlesville, Okla.

[21] Appl. No.: 666,163

[22] Filed: Feb. 26, 1991

[51] Int. Cl.$^5$ .............................................. G01R 33/20
[52] U.S. Cl. .................................................... 324/307
[58] Field of Search .................... 378/5; 73/61.1 R; 324/300, 303, 307, 318, 322

[56] References Cited

U.S. PATENT DOCUMENTS

| | | | |
|---|---|---|---|
| 4,291,271 | 9/1981 | Lauffer | 324/307 |
| 4,424,487 | 1/1984 | Lauffer | 324/307 |
| 4,493,039 | 1/1985 | Gregory | 324/300 |
| 4,542,343 | 9/1985 | Brown | 324/307 |
| 4,649,483 | 3/1987 | Dixon, Jr. | 378/5 |
| 4,671,102 | 6/1987 | Vinegar et al. | 73/61.1 R |
| 4,728,892 | 3/1988 | Vinegar et al. | 324/309 |
| 4,868,500 | 9/1989 | Baldwin et al. | 324/307 |

OTHER PUBLICATIONS

Baldwin, B. A. et al., "Detecting Fluid Movements and Isolation in Reservoir Cores Using Medical NMR Imaging Techniques", Society of Petroleum Engineers/Department of Energy 14884, SPE/DOE Fifth Symposium on Enhanced Oil Recovery (1986), pp. 39–42 and Figures.

Baldwin, B. A. et al., "Determining Fluid Saturation Distribution in Cores Using NMR Imaging", *The Log Analyst*, vol. 28, No. 2 (Mar.–Apr. 1987), p. 194.

Timur, A., "Pulsed Nuclear Magnetic Resonance Studies of Porosity, Movable Fluid, and Permeability of Sandstone" *Journal of Petroleum Technology* (Jun. 1969) pp. 775–786.

Brown, R. J. S. et al., "Measurements of Fractional Wettability of Oilfield Rocks By the Nuclear Magnetic Relaxation Method", *Petroleum Transactions*, AIME, vol. 207 (1956).

"CSI Applications", General Electric Bulletin, General Electric Company, NMR Instruments, Fremont, Calif.

Bottomley, P. A., "NMR Imaging Techniques and Applications: A Review", *Rev. Sci. Instrum.*, 53(9), (Sep. 1982), pp. 1319–1337.

Andrew, R. E., "NMR Imaging", *Acc. Chem. Res.*, vol. 16 (1983), pp. 114–122.

Fullerton, G. C. et al., "Nuclear Magnetic Resonance Imaging in Biological Systems", *Bio Techniques*, vol. 3, No. 6 (1985), pp. 458–465.

Wharry, S. M. et al., "Interfacing a Microcomputer and Robot to a Pulsed NMR Spectrometer", *American Laboratory*, Sep. 1985.

Amott, Earl, "Observations Relating to the Wettability of Porous Rock". *Petroleum Transactions*, AIME, vol. 216, 1959, pp. 156–162. T. P. 8069.

Primary Examiner—Michael J. Tokar
Attorney, Agent, or Firm—William R. Sharp

[57] ABSTRACT

A method is provided for determining the relative wettability of a sample of a porous media with respect to a first liquid and a second liquid. The method includes the steps of providing the sample at a partially saturated state with respect to the first liquid; obtaining a first nuclear magnetic resonance (NMR) parameter value for the partially saturated sample; exposing the partially saturated sample to the second liquid for a predetermined period of time, wherein the second liquid is treated with a paramagnetic species such that the presence of the second liquid in the sample does not substantially affect the NMR signal response of the sample; obtaining a second NMR parameter value for the sample after exposure to the second liquid; and determining the relative wettability by comparing the first and second NMR parameter values.

13 Claims, 4 Drawing Sheets

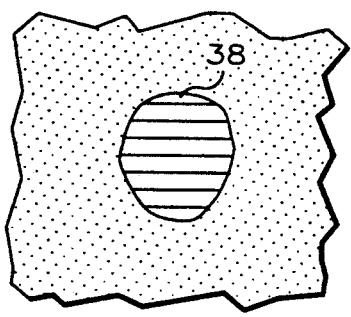
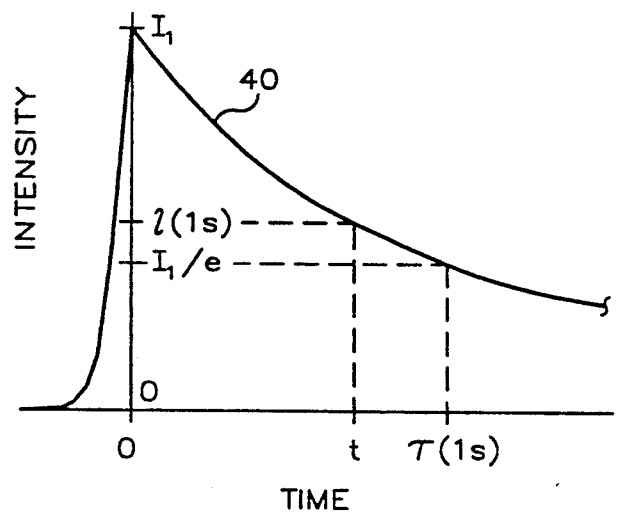
*FIG. 4A*  *FIG. 4B*
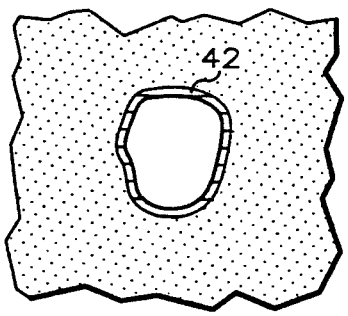
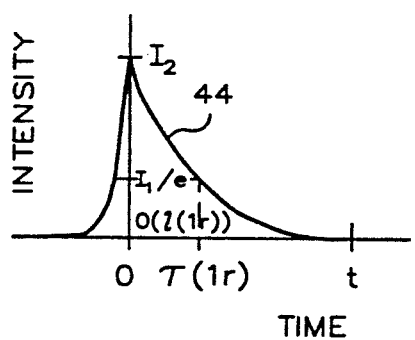
*FIG. 5A*  *FIG. 5B*

METHOD FOR DETERMINING RELATIVE WETTABILITY

BACKGROUND OF THE INVENTION

This invention relates to a method for determining the relative wettability of a sample of a porous media with respect to two different liquids.

Wettability of a solid substance with respect to a particular liquid is a measure of the interaction of the liquid with the surfaces of the substance. In other words, wettability is a measure of the strength of adhesion of a liquid to surfaces with which it is in contact.

The relative wettability of a solid substance with respect to a first liquid and a second liquid refers to the comparison of the substance's wettability with respect to the first and second liquids. The relative wettability of a subterranean formation, made up of a porous media such as rock, with respect to oil and water is an important property in determining the suitability of the formation for secondary recovery of oil by waterflooding. Generally, waterflooding of a formation will be desirable only if that formation is water wettable; that is, is more wettable with respect to water than oil.

Heretofore, the primary method used to determine relative wettability of a sample of a porous media (i.e. core plug) with respect to oil and water is the relative displacement method of Ammott, described in Trans. AIME, vol. 216, pp. 156-162 (1959). This method generally involves displacement of oil and water from a core plug, and comprises a series of labor intensive steps which include centrifuging of the core plug to drive liquid therefrom. Liquid, therefore, must flow through and from the core plug. Consequently, accuracy of the method depends not only on interaction of surfaces of the core plug with either the oil or water, but also on the pore and pore throat (passages between pores) sizes and geometry. Moreover, it is difficult to apply the Ammott method to core plugs which are fractured or fragile.

SUMMARY OF THE INVENTION

It is, therefore, an object of the invention to provide an improved method for determining relative wettability of a sample of a porous media with respect to two different liquids.

It is another object of the invention to provide a method for determining relative wettability of a sample which does not involve centrifuging of the sample, thereby avoiding problems associated therewith which are discussed above.

The above objects are realized by a method for determining the relative wettability of a sample of a porous media with respect to a first liquid and a second liquid comprising: (a) providing the sample at a saturation with respect to the first liquid which is less than fully saturated; (b) subjecting the sample at the above-mentioned saturation to a static magnetic field and a pulsed radio frequency field such that at least one nuclear magnetic resonance (NMR) signal results which has associated therewith amplitude which decays over time from a maximum at a corresponding time; (c) determining with respect to the NMR signal(s) from (b) at least one NMR parameter which is selected from (1) amplitude at a preselected delay time after the time at which intensity is at its maximum or (2) the time at which amplitude is at a predetermined fraction of its maximum, thereby yielding at least one first NMR parameter value; (d) exposing the sample after step (b) to the second liquid for a predetermined period of time, wherein the second liquid is treated with a paramagnetic species such that the presence of the second liquid in the sample does not substantially affect the NMR signal response of the sample; (e) subjecting the sample after step (d) to substantially the same static and pulsed radio frequency fields as employed in (b) to result in at least one NMR signal which has associated therewith amplitude which decays over time from a maximum at a corresponding time; (f) determining at least one NMR parameter for the NMR signal(s) from (e), thereby yielding at least one second NMR parameter value; and (g) determining the relative wettability by comparing the first and second NMR parameter values.

According to a preferred embodiment described in detail hereafter, the method of the invention is applied to a core plug as the sample, wherein the method further comprises cleaning the core plug after step (e) so as to remove substantially all of the first and second liquids therefrom, obtaining additional NMR parameter values corresponding to the core plug less than fully saturated with the second liquid and after exposure to the first liquid, and determining a wettability index based on the various NMR parameter values.

BRIEF DESCRIPTION OF THE DRAWINGS

FIGS. 4A, 4B, 5A, 5B, 6A, 6B, 7A, and 7B illustrate typical nuclear magnetic resonance (NMR) signal responses for a core plug at different points of one embodiment of the method in accordance with the invention, and further illustrate a partial cross section of the core plug and a pore therein at such points of the method.

DETAILED DESCRIPTION OF THE INVENTION

A particular embodiment of the invention will now be described in which relative wettability of a core plug is determined with respect to oil and water. It should be understood, however, that the invention could be applied to any sample of a porous media and any liquids.

Several terms which are used repeatedly through the following description and in the appended claims are defined below:

The term "saturation" with respect to a particular liquid in a porous media refers to the portion (i.e. in terms of a fraction or percent) of pore volume in the porous media which is filled with that liquid. A porous media which is 100% saturated has all its pore volume filled with liquid.

The term "residual saturation" is a state of saturation reached after the porous media is subjected to a technique for driving liquid from the porous media for a sufficient length of time until liquid flow from the porous media terminates. Depending on the particular porous media, liquid and desaturation technique employed, residual saturations typically are in the range of about 10% to about 40%.

The term "nuclear magnetic resonance" is hereinafter expressed as NMR.

Figure 1:
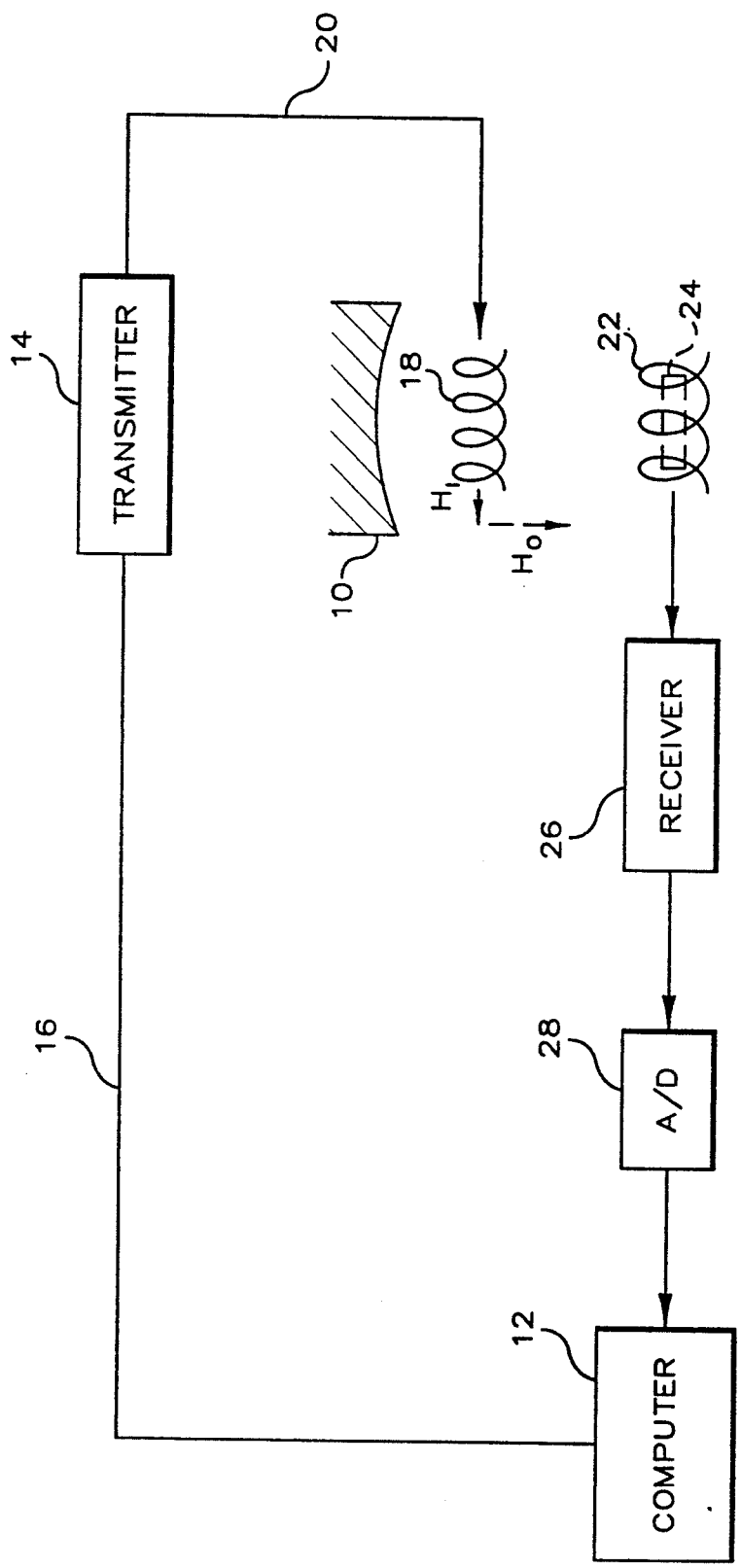
FIG. 1 is a schematic illustration of an apparatus for use in the present invention.

Referring to FIG. 1, there is shown one embodiment of an apparatus which can be used to practice the invention. The apparatus includes a resistive, permanent or superconducting, preferably superconducting, magnet 10 which produces a static magnetic field $H_0$ in the indicated direction. The apparatus further includes a computer 12 which has the capability of controlling radio frequency transmitter 14 via signal line 16, and which can further have the capability to process incoming data if desired. Transmitter 14 is adapted to produce radio frequency signals at a predetermined frequency which are received by RF coil 18 via signal line 20. RF coil 18 accordingly generates a radio frequency field $H_1$ in a direction perpendicular to $H_0$ in the form of a single pulse or sequence of pulses in response to commands from suitably programmed computer 12. Also shown in FIG. 1 is a receiver coil 22 which comprises a suitable conductor, such as copper. Core plug 24 is shown as being generally coaxially positioned within receiver coil 22. Receiver coil 22 functions as an NMR detector in a manner discussed further below so as to produce at least one signal which is received by and appropriately amplified by receiver 26. The amplified signal is digitized by A/D converter 28 and fed into computer 12 for processing.

It should be also understood that the relative positions of receiver coil 22, magnet 10 and RF coil 18 are not necessarily as illustrated, but are rather depicted in FIG. 1 for clarity of illustration.

A commercially available NMR system can be used for the apparatus of FIG. 1. One possible system can include the IBM PC-20 NMR spectrometer, in which case core plug 24 can be contained in a glass tube which is appropriately positioned within receiver coil 22. Such an NMR spectrometer can be coupled with a personal computer in the manner discussed in an article entitled "Interfacing a Micro Computer and Robot to a Pulsed NMR Spectrometer" by S. M. Wharry et al, *American Laboratory* (September 1985), which is hereby incorporated by reference.

The receiver coil 22 of FIG. 1 produces at least one signal corresponding to the entire core plug 24. Such a system is suitable for smaller core plugs of less than, for example, about 1 cm$^3$ in volume, but larger core plugs may require a more sophisticated system having gradient coils for scanning multiple volume elements of the core plug. Signals would in that case be produced for a plurality of volume elements in the core plug which could then be averaged in the manner discussed in a subsequent example. A commercially available system with such scanning capability is discussed further in the Example.

In order to produce an NMR signal in receiver coil 22, core plug 24 is subjected to the static magnetic field $H_0$ as produced by magnet 10. Spinning nuclei of liquid in the core plug act as magnetic dipoles which are caused to align with the static magnetic field such that the magnetization vectors associated with the spinning nuclei precess at a certain precessional frequency around axes which are parallel to the direction of the static field. The core plug 24 is also subjected to a radio frequency field $H_1$ as generated by RF coil 18. The frequency selected must be the resonant frequency. That is, the frequency must be equivalent to the precessional frequency of the spinning nuclei so as to achieve resonance. For the purpose of the particular embodiment described herein employing oil and water, it is most convenient to use a resonant frequency with respect to hydrogen nuclei which are common to both oil and water. Generally, the radio frequency field is applied to the core plug as a pulse or sequence of pulses only a few milliseconds in duration. It is presently preferred to employ a single 90° pulse as is explained further below.

Figure 2:
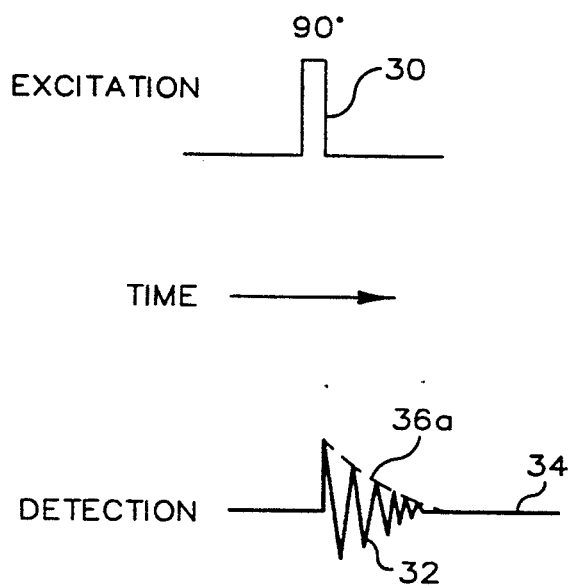
FIG. 2 depicts a radio frequency pulse and a detected signal according to one embodiment of the invention.

Referring to FIG. 2, a pulse 30 is applied of sufficient amplitude and duration to cause the precessional axes of the precessing nuclei to rotate 90° to a nonequilibrium, excited state which causes a voltage to be induced in the receiver coil. The resulting signal is shown at 32, which is sometimes called an FID (free induction decay) signal. The amplitude, or variation in magnitude of the signal with respect to base line 34, can be seen to decay over time from a maximum as is indicated by the broken line at 36a. The amplitude of signal 32 as a function of time is stored in computer 12 as a series of digitized, unitless "intensity" values representative of amplitude at corresponding time values. Hereinafter, in the Detailed Description of the Invention, the term "intensity" will be used rather than "amplitude" since the preferred embodiment described herein is in terms of typical commercial NMR instruments which store and produce as outputs the unitless intensity value.

Figure 3:
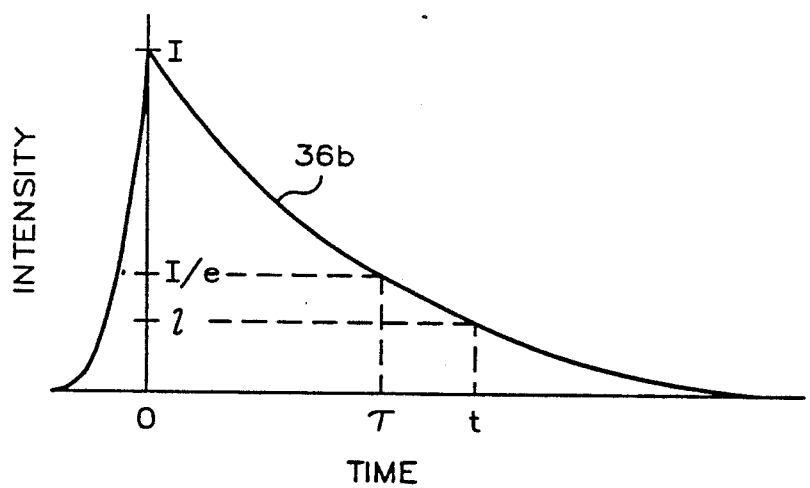
FIG. 3 illustrates the amplitude ("intensity") as a function of time for the detected signal shown in FIG. 2.

Curve 36a from FIG. 2 is shown on an enlarged scale at 36b in FIG. 3. As shown, curve 36b indicates the relationship between intensity and time, wherein intensity decays from a maximum of I at a time which is set at 0 in the illustrated graph. An NMR parameter, discussed further below with respect to the method of the invention, can be determined from the graph of FIG. 3 by selecting either (1) an intensity at a preselected delay time or (2) the time at which the intensity is at a predetermined fraction of its maximum value I. With respect to (1), the preselected delay time is indicated in FIG. 3 to be at time t, at which the NMR parameter in terms of intensity is indicated by the symbol $\iota$. As to (2), the predetermined fraction of maximum intensity I can be assumed to be 1/e, whereby the NMR parameter in terms of time is indicated by the symbol $\iota$. From elementary mathematics e=2.71828. The time taken to decay from maximum intensity I to intensity I/e is sometimes referred to as the "relaxation time".

Although the single 90° pulse and consequent FID signal is particularly convenient in accordance with the invention because of its simplicity, other pulses or pulse sequences which produce at least one NMR signal which decays in intensity from a maximum value is within the scope of the present invention. For example, another pulse sequence, called the Hahn spin echo sequence, involves a 90° pulse followed by a 180° pulse which produces a "spin echo" NMR signal following the 180° pulse.

A preferred embodiment of the method of the invention will now be described with reference to FIGS. 3–7. Each such FIGURE has a corresponding "A" FIGURE which shows the state of a particular pore in the core plug, and a corresponding "B" FIGURE which shows the NMR signal response for the core plug. The illustrations shown are solely for the purpose of facilitating an understanding of the invention. The graphs of intensity versus time do not correspond to any actual NMR data, and the pore illustrations are merely schematic representations which are not necessarily shown to scale. Such pore illustrations further assume that the pore is sufficiently large so as to not be completely filled when containing an adsorbed layer of liquid on its inner surface. In addition, in each step noted below in which an NMR parameter value is obtained, it is to be understood that such step involves subjecting the core plug to the static and RF fields discussed above, and determining the NMR parameter value from the resulting NMR signal. It is assumed that for each NMR parameter value obtained, the static and RF fields are substantially the same and further that the RF field is applied in a particular pulse sequence, such as the 90° signal described above, to result in an NMR signal which decays in intensity from a maximum value.

1. Clean Core Plug to Remove Oil and Water Therein

The core plug is cleaned in suitable solvents for water and oil, such as methanol and toluene, respectively. A mixture of such solvents could be employed or each solvent could be used in sequence. The cleaning process involves pumping the solvents through the core plug for a predetermined number of pore volumes to flush out the oil and/or water therein. After cleaning, the core plug is preferably dried in a suitable oven to remove residual solvent and then cooled in a desiccator.

2. Saturate Core Plug with Oil

For the sake of illustration, the core plug is first saturated with oil in this particular embodiment, although it should be understood that the core plug could alternatively be first saturated with water. The oil employed can be any suitable liquid hydrocarbon, such as, for example, heptadecane.

The core plug can be saturated by any suitable technique such as the flash saturation technique. According to such a technique, the core plug is placed in a flask and the flask is evacuated to very low pressure, followed by injection of the saturating liquid into the flask so as to immerse the core plug in the liquid. Atmospheric pressure is then restored to the flask so as to cause a sudden change in pressure and force liquid into the pores of the core plug, typically resulting in a substantially saturated state of at least 99%. It is preferred that the core plug be as close to 100% saturation as possible. The core plug can also be saturated by flowing the saturating liquid therethrough.

Referring to FIG. 4A, the illustrated pore is shown as being completely filled with oil, as indicated by the solid cross hatching at 38, after the above described saturation procedure.

3. Obtain NMR Parameter Value for Saturated Core Plug

An NMR signal is generated for the substantially saturated core plug. Referring to FIG. 4B, curve 40 indicates the relationship between intensity and time for such an NMR signal as it decays from a maximum value of $I_1$. The NMR parameter can be selected as $\iota(1s)$, which is the intensity at a preselected delay time t (which is preferably selected such that $\iota(1s)$ is greater than 0), or $\tau(1s)$, which is the time at which intensity is 1/e of its maximum value, or $I_1/e$.

4. Desaturate Core Plug

The core plug is now desaturated with respect to oil, preferably to residual saturation, by any suitable technique. For example, the core plug can be desaturated by the "porous plate" method in which the core plug is positioned on a porous plate within a pressure chamber pressurized with an inert gas. The pressurized inert gas acts to force liquid from the core plug, which passes through the porous plate and is accordingly collected. Alternatively, the core plug can be desaturated by centrifuging.

Referring to FIG. 5A, a thin film of oil as schematically indicated at 42 is absorbed to the surface which defines the pore.

For certain calculations discussed further below, it is necessary to determine the saturation level of the core plug with respect to oil in its desaturated state, hereinafter referred to as R(1). R(1) can be expressed as a fraction or percentage, but is hereafter assumed to be a fraction. Such saturation can be determined by any suitable technique. One technique employs measured weights of the core plug, wherein the saturation level of the core plug in its desaturated state is given by $(W_3 - W_1)/(W_2 - W_1)$, where $W_1$ is the weight of core plug after cleaning and drying in step 1, $W_2$ is the weight of the core plug after substantial saturation thereof in step 2, and $W_3$ is the weight of the desaturated core plug in this step 4.

5. Obtain NMR Parameter Value for Desaturated Core Plug

An NMR signal is generated for the desaturated core plug. Referring to FIG. 5B, curve 44 indicates the relationship between intensity and time for such an NMR signal as it decays from a maximum intensity $I_2$. The NMR parameter value for the desaturated core plug can accordingly be selected as either $\iota(1r)$, which is the intensity (0 in this particular embodiment) at delay time t, or $\tau(1r)$ which is the time at which intensity is 1/e of $I_2$, or $I_2/e$.

In comparing the graphs for FIGS. 4B and 5B, it can be seen that the maximum intensity for the desaturated core plug is less than that for the saturated core plug since intensity is related to the saturation of the core plug. Furthermore, curve 44 decreases or decays in intensity as a function of time at a faster rate than in curve 40. Therefore, $\iota(1r)$ and $\tau(1r)$ are less than $\iota(1s)$ and $\tau(1s)$, respectively, due to the decrease in saturation and due to the increase in decay rate. The above-mentioned difference in decay rate between curves 40 and 44 is believed to occur because the rate of decay of an intensity versus time curve is generally decreased by the presence of liquid in the "bulk" or interior of the pore out of contact with the surface defining the pore. Once the liquid is removed from the interior of the pore, leaving only a film as shown in FIG. 5A, the rate of decay of the intensity versus time curve is maximized, thus minimizing the intensity at a preselected delay time or the time at which intensity is at a preselected fraction of maximum intensity.

6. Expose Desaturated Core Plug to Water So As to "Flood" Plug

The water employed in this step can be fresh water or "brine" comprising primarily water and a minor portion of salt dissolved therein. In accordance with the invention, the water as used in this step contains a paramagnetic species in a sufficient concentration that water remaining in the core plug after this step does not substantially affect the NMR signal response of the core plug. Suitable paramagnetic species for use in accordance with the invention include nickel(II) compounds, manganese(IV) compounds and iron compounds which are soluble in water but not in oil. A particularly preferred compound is manganese dichloride. The concentration of the paramagnetic species in the water can vary widely from a few ppm to greater than 10,000 ppm, more typically in the range of about 500 ppm to about 4000 ppm, depending, for example, upon the composition of the particular oil employed and its associated NMR signal response. In any event, the concentration of the paramagnetic species is such that the NMR signal response associated with the water containing the paramagnetic species decays in intensity with respect to time at a sufficiently rapid rate so as to not substantially affect or interfere with the NMR signal response produced as a result of the oil contained in the core plug.

The desaturated core plug can be exposed to the paramagnetic treated water by simply immersing the core plug therein for a period of time of, for example, about one to about three days, or by immersing the core plug in the paramagnetic treated water in conjunction with the flash saturation technique described previously to preferably result in a "flooded" core plug which is substantially saturated with liquid (both water and oil).

Figure 6A:
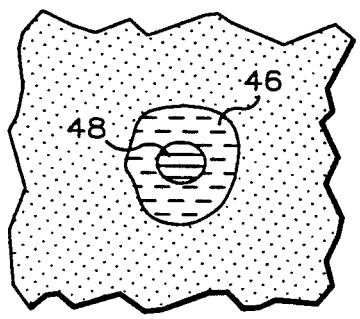
Figure 7A:
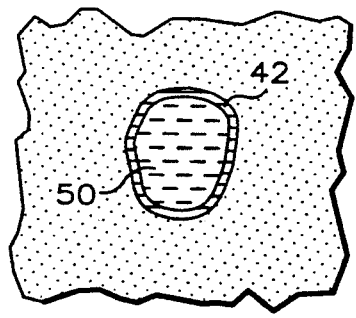

The result of the above described step will now be considered with respect to the two extreme cases, wherein the core plug is strongly wettable with respect to water or strongly wettable with respect to oil.

Where the core plug is strongly water wettable, the water will act to displace the oil from the surface defining the pores so as to result in a condition as illustrated in FIG. 6A. In FIG. 6A, the water is indicated at 46 by the broken cross hatching to be in contact with the surface defining the pore and to surround the oil, which is indicated at 48. In this extreme case, the water clearly interacts with the surface defining the pore so as to be tightly bound thereto, forcing the oil to a position within the interior of the pore.

Where the core plug is strongly oil wettable, the oil would remain absorbed as a thin film upon the surface defining the pore as indicated at 42 in FIG. 7A, and the water would assume a position within the interior of the pore as indicated at 50.

7. Obtain NMR Parameter Value for Flooded Core Plug

Figure 6B:
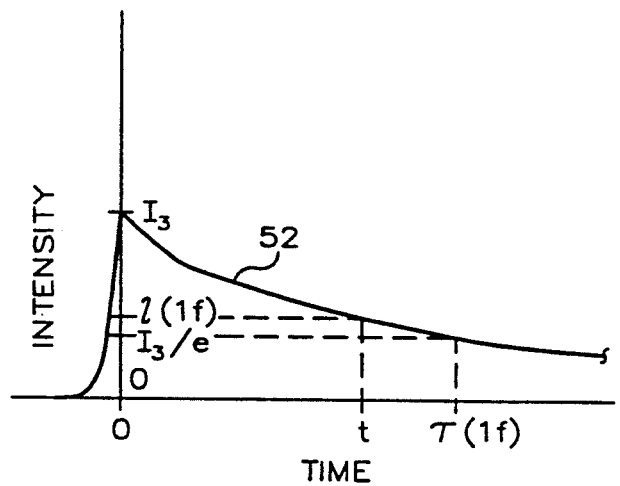
Figure 7B:
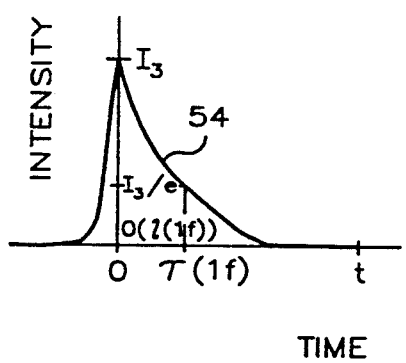

An NMR signal is generated for the flooded core plug. Intensity as a function of time for the decaying NMR signal is illustrated in FIGS. 6B and 7B with respect to the strongly water wettable and strongly oil wettable cases, respectively. In each case, intensity decays from a maximum of $I_3$.

With respect to curve 52 in FIG. 6B, intensity decays with respect to time more slowly than for either of curves 40 or 44 of FIGS. 4B and 5B, respectively, due to the fact that the oil is positioned solely in the interior of the pore out of contact with the surface defining the pore, thereby minimizing the decay rate. In addition, the maximum intensity $I_3$ for curve 52 is lower, by a factor of approximately $R(1)$, than maximum intensity $I_1$ for curve 40 because of the lower saturation associated with curve 52, but is about the same as maximum intensity $I_2$ for curve 44 because of the same saturation. The NMR parameter value is selected from either $\iota(1f)$, which is the intensity at delay time t, or $\tau(1f)$, which is the time at which intensity is $1/e$ of $I_3$, or $I_3/e$.

The following expressions apply to the strongly water wettable case, wherein the symbol $\approx$ means approximately equal to:

$$\iota(1f) \approx R(1) \times \iota(1s), \text{ and} \tag{1}$$

$$\tau(1f) \approx \tau(1s). \tag{2}$$

With respect to the strongly oil wettable case, reference is made to FIG. 7B which shows curve 54 as being substantially identical to curve 44 of FIG. 5B. Curve 54 remains essentially unchanged from curve 44 since the oil in the strongly oil wettable case does not change in position and remains in contact with the surface defining the pore. Therefore, the following expressions (3) and (4) apply to the strongly oil wettable case:

$$\iota(1f) \approx \iota(1r), \text{ and} \tag{3}$$

$$\tau(1f) \approx \tau(1r). \tag{4}$$

Expressions (1) and (2) define the upper boundary for the NMR parameter, and expressions (3) and (4) define the lower boundary for the NMR parameter. Therefore, with respect to intensity as the NMR parameter, the following relationship expresses the upper and lower boundaries of $I(1f)$:

$$R(1) \times \iota(1s) \gtrsim \iota(1f) \approx \iota(1r). \tag{5}$$

Expression (5) can be rewritten as follows:

$$1 \gtrsim \frac{\iota(1f) - \iota(1r)}{R(1) \times \iota(1s) - \iota(1r)} \gtrsim 0. \tag{6}$$

Similarly, the following expression defines the upper and lower boundaries of $\tau(1f)$:

$$\tau(1s) \gtrsim \tau(1f) \approx \tau(1r). \tag{7}$$

Expression (7) can be rewritten as follows:

$$1 \gtrsim \frac{\tau(1f) - \tau(1r)}{\tau(1s) - \tau(1r)} \gtrsim 0. \tag{8}$$

In each of expressions (6) and (8), the value 1 corresponds to a strongly water wettable core plug and the value 0 corresponds to a strongly oil wettable core plug.

8. Clean Core Plug to Remove Water and Oil

The core plug is again cleaned to remove oil and water therefrom in the same manner as described in step 1.

9. Repeat Steps 2–7 with Respect to Water as Saturating Liquid and Oil as Flooding Liquid The above-mentioned steps are repeated with the liquids reversed, wherein such steps comprise the following: saturating the core plug with water; obtaining an NMR parameter value $\iota(2s)$ or $\tau(2s)$ for the saturated core plug; desaturating the core plug with respect to water, preferably to residual saturation $R(2)$; obtaining an NMR parameter value $\iota(2r)$ or $\tau(2r)$ for the desaturated core plug; exposing the desaturated core plug to oil as the "flooding" liquid; and obtaining an NMR parameter value $\iota(2f)$ or $\tau(2f)$ for the flooded core plug. In flooding the core plug with oil, the oil is treated with a suitable paramagnetic species soluble therein but not in water and in a sufficient amount such that the presence of the oil in the core plug does not substantially affect the NMR signal response of the core plug. A particularly suitable paramagnetic species is ferrocene ($FeC_6$). Concentration of the paramagnetic species in the oil can vary widely between a few ppm to about 20,000 ppm, more typically in the range of about 1000 ppm to about 8000 ppm. With regard to relating the various NMR parameter values, the following expressions can be derived which are similar to expressions (6) and (8) above:

$$1 \gtrsim \frac{\iota(2f) - \iota(2r)}{R(2) \times \iota(2s) - \iota(2r)} \gtrsim 0, \tag{9}$$

-continued and $$1 \gtrsim \frac{\tau(2f) - \tau(2r)}{\tau(2s) - \tau(2r)} \gtrsim 0, \quad (10)$$

wherein the value 1 corresponds to a strongly oil wettable core plug and the value 0 corresponds to a strongly water wettable core plug.

10. Determine Relative Wettability Index W

A relative wettability index W can be determined in terms of intensity by combining expressions (6) and (9) to give:

$$W = \frac{\iota(1f) - \iota(1r)}{R(1) \times \iota(1s) - \iota(1r)} - \frac{\iota(2f) - \iota(2r)}{R(2) \times \iota(2s) - \iota(2r)}. \quad (11)$$

Similarly, expressions (8) and (10) can be combined to give an expression for the wettability index W in terms of time:

$$W = \frac{\tau(1f) - \tau(1r)}{\tau(1s) - \tau(1r)} - \frac{\tau(2f) - \tau(2r)}{\tau(2s) - \tau(2r)}. \quad (12)$$

In either expression (11) or (12) for the wettability index W, $-1 \leq W \leq 1$, where $-1$ corresponds to a strongly oil wettable core plug, 0 corresponds to a core plug having generally neutral wettability, and 1 corresponds to a strongly water wettable core plug.

Example

The purpose of this example is to demonstrate the effectiveness of the invention in determining the relative wettability of a core plug with respect to oil and water. This example is provided to further illustrate the invention, and should not be construed to limit the invention in any manner.

A modified Picker International MR VISTA 2055 NMR System, including the elements shown in FIG. 1 and also gradient coils to scan the core plug, was employed in this example to obtain the various NMR data. The commercially available system was modified to have a receiver coil which approximates the size of the core plug being tested. Referring to FIG. 1, the receiver coil 22 was 5 inches in length, 2 inches in inside diameter, and consisted of 4.5 turns of ⅛ inch copper tubing. A Teflon ® tubular member served as a support for the copper tubing, which was wrapped around the tubular member in grooves on its exterior surface, and was positioned on a Plexiglas stand so as to be approximately centered within RF coil 18. In addition, the tubular member had an inside diameter to receive the core plug 24 therein so as to be approximately coaxially positioned within receiver coil 22. Finally, the Picker International Unit employed a superconducting magnet.

As noted above, the NMR system of this example included gradient coils for scanning capability. Volume elements or voxels in the core plug were scanned such that a spin echo signal was generated for each voxel. Important NMR operating conditions were as follows: a spin echo time (time between 90° and 180° pulses) of 26 milliseconds; an individual voxel size of 0.5 mm×0.5 mm×5 mm; a static field strength of 0.5 Tesla; a gradient field strength of 3 Gauss/meter; and an RF frequency of 21.3 MHz.

The procedure performed will now be described. In carrying out the procedure, the core plug was contained in a polyethylene bag to assist in preventing evaporation of liquid from the core plug. The polyethylene bag is transparent to the fields employed.

A core plug of Berea sandstone (about 22% porosity and about 600 millidarcy permeability) having a length of 2 inches and a diameter of 15/16 inch was selected for testing. The liquids used in this example were heptadecane and brine solution comprising 2.0 wt % sodium chloride and 98.0% distilled water.

Steps 1–7 as described previously were carried out. In step 1, the core plug was cleaned with methanol and toluene. In step 2, the core plug was saturated with heptadecane to about 97% saturation using the flask saturation technique. In each of steps 3, 5 and 7 in which NMR parameter values are obtained, an NMR spin echo signal was generated for each voxel of a plurality of voxels along a transaxial 5 mm thick slice along the core longitudinal axis, and an average intensity value was obtained by averaging the voxel intensities corresponding to a cluster of voxels in the slice which defined an area of about 1.3 cm² near the center of the core plug. The intensity value for each NMR signal was taken to be the intensity of the signal at a delay time of 26 milliseconds after intensity is at its maximum. Accordingly, steps 3, 5 and 7 resulted in the following NMR parameter values in terms of unitless "counts": $\iota(1s)=963$; $\iota(1r)=0$; and $\iota(1f)=216$. In step 4, the core plug was desaturated to residual saturation (determined to be 0.224 or 22.4% by the weighing technique described in step 4) by centrifuging at 4000 RPM for about 2 hours until equilibrium was reached and flow of heptadecane from the core plug terminated. In step 6, the brine was treated with 4000 ppm manganese dichloride and allowed to flood the core plug by the flask saturation technique.

The values for $\iota(1s)$, $\iota(1r)$, $\iota(1f)$ and R(1) were substituted into expression (6) to give a value of 1.0, which indicates the core plug to be strongly water wettable, and therefore a strong candidate for waterflooding.

CONCLUSION

Thus, there is provided by the present invention a method for effectively determining the relative wettability of a sample of a porous media with respect to two different liquids. The method of the invention is advantageous over prior methods, such as the previously described Ammott method, in that its results are not affected by the pore and pore throat sizes and geometry but instead are primarily dependent on the interaction of the liquid with surfaces of the porous media.

Obviously many modifications and variations of the present invention are possible in light of the above teachings. For example, the method of the invention can be practiced qualitatively without actually calculating a wettability index. According to such an embodiment, an image of the sample can be generated on a CRT screen based on a plurality of NMR parameter values obtained in each of steps 3, 5 and 7 by means of a scanning NMR system. Such images can then be compared to determine whether the sample is more wettable by one liquid or the other liquid. It is, therefore, to be understood that within the scope of the appended claims the invention may be practiced otherwise than as specifically described.

That which is claimed is:

1. A method for determining the relative wettability of a sample of a porous media with respect to a first liquid and a second liquid comprising:
   (a) providing the sample at a saturation with respect to the first liquid which is less than fully saturated;
   (b) subjecting the sample at said saturation to a static magnetic field and a pulsed radio frequency field such that at least one NMR signal results which has associated therewith amplitude which decays over time from a maximum at a corresponding time;
   (c) determining with respect to said at least one NMR signal from (b) at least one NMR parameter which is selected from amplitude at a preselected delay time after said corresponding time or the time after said corresponding time at which amplitude is at a predetermined fraction of its maximum, thereby yielding at least one first NMR parameter value;
   (d) exposing the sample after step (b) to the second liquid for a predetermined period of time, wherein the second liquid is treated with a paramagnetic species such that the presence of the second liquid in the sample does not substantially affect the NMR signal response of the sample;
   (e) subjecting the sample after step (d) to substantially the same static and pulsed radio frequency fields as employed in (b) to result in at least one NMR signal which has associated therewith an amplitude which decays over time from a maximum at a corresponding time;
   (f) determining at least one NMR parameter for said at least one signal from (e), thereby yielding at least one second NMR parameter value; and
   (g) determining the relative wettability by comparing the first and second NMR parameter values.

2. A method as recited in claim 1 further comprising the steps:
   (h) cleaning the sample after step (e) so as to remove substantially all of the first and second liquids therefrom;
   (i) providing the sample after step (h) at a saturation with respect to the second liquid which is less than fully saturated;
   (j) subjecting the sample at said saturation in (i) to substantially the same static magnetic and pulsed radio frequency fields as employed in (b) such that at least one NMR signal results which has associated therewith amplitude that decays over time from a maximum at a corresponding time;
   (k) determining for said at least one NMR signal from (j) at least one NMR parameter, thereby yielding at least one third NMR parameter value;
   (l) exposing the sample after step (j) to the first liquid for a predetermined period of time, wherein the first liquid is treated with a paramagnetic species such that the presence of the first fluid in the sample does not substantially affect the NMR signal response of the sample;
   (m) subjecting the sample after step (1) to substantially the same static and pulsed radio frequency fields as employed in (b) to result in at least one NMR signal which has associated therewith amplitude which decays over time from a maximum at a corresponding time;
   (n) determining at least one NMR parameter for said at least one signal from (m), thereby yielding at least one fourth NMR parameter value; and
   wherein step (g) is performed after step (n) such that the third and fourth NMR parameter values are also compared, and wherein the relative wettability is determined by combining the comparison of the first and second NMR parameter values and the comparison of the third and fourth NMR parameter values.

3. A method as recited in claim 2 wherein in each of steps (a) and (i) the sample is substantially saturated with the respective liquid, followed by desaturating the sample to residual saturation.

4. A sample as recited in claim 3 further comprising:
   (o) subjecting the sample in its substantially saturated state in step (a) to substantially the same static magnetic and radio frequency fields as employed in step (b) such that at least one NMR signal results which has associated therewith amplitude which decays over time from a maximum at a corresponding time;
   (p) determining with respect to said at least one NMR signal from (o) at least one NMR parameter, thereby yielding at least one fifth NMR parameter value;
   (q) subjecting the sample in its substantially saturated state in step (i) substantially the same static magnetic and radio frequency fields as employed in step (b) such that at least one NMR signal results which has associated therewith amplitude which decays over time from a maximum at a corresponding time;
   (r) determining with respect to said at least one NMR signal from (q) at least one NMR parameter, thereby yielding at least one sixth NMR parameter value; and
   wherein in step (g) the fifth and sixth NMR parameter values are incorporated into the determination of the relative wettability.

5. A method as recited in claim 4 wherein in each of steps (c), (f), (k), (n), (p) and (r), a single NMR parameter value is determined, and in step (g) each of the NMR parameter values are employed to derive a wettability index W, where $-1 \geq W \geq 1$.

6. A method as recited in claim 5 wherein in each of steps (c), (f), (k), (n), (p) and (r) the NMR parameter is amplitude at a preselected delay time and wherein in such steps the first, second, third, fourth, fifth and sixth NMR parameters are hereafter denoted as $\iota(1r)$, $\iota(1f)$, $\iota(2r)$, $\iota(2f)$, $\iota(1s)$ and $\iota(2s)$, respectively, and wherein said method further comprises determining the residual saturation in steps (a) and (i) which are hereafter denoted as $R(1)$ and $R(2)$, respectively.

7. A method as recited in claim 6 wherein in step (g), the relative wettability index W is determined from the following expression:

$$W = \frac{\iota(1f) - \iota(1r)}{R(1) \times \iota(1s) - \iota(1r)} - \frac{\iota(2f) - \iota(2r)}{R(2) \times \iota(2s) - \iota(2r)}.$$

8. A method as recited in claim 5 wherein in each of steps (c), (f), (k), (n), (o) and (r) the NMR parameter is time at a preselected fraction of maximum amplitude and wherein in such steps the first, second, third, fourth, fifth and sixth NMR parameter values are hereafter denoted as $\tau(1r)$, $\tau(1f)$, $\tau(2r)$, $\tau(2f)$, $\tau(1s)$ and $\tau(2s)$.

9. A method as recited in claim 8 wherein in step (g) the relative wettability index W is determined from the following expression:

$$W = \frac{\tau(1f) - \tau(1r)}{\tau(1s) - \tau(1r)} - \frac{\tau(2f) - \tau(2r)}{\tau(2s) - \tau(2r)}.$$

10. A method as recited in claim 5 wherein in each of steps (d) and (l) the sample is immersed in second liquid and first liquid, respectively, whereby at the end of such steps the sample is substantially saturated with liquid.

11. A method as recited in claim 10 wherein in each of steps (b), (e), (j), (m), (o) and (q) said at least one NMR signal in each such step comprises a free induction decay signal.

12. A method as recited in claim 11 wherein the sample is a core plug.

13. A method as recited in claim 12 wherein the first liquid is one of oil and water and the second liquid is the other liquid.

* * * * *

UNITED STATES PATENT AND TRADEMARK OFFICE
CERTIFICATE OF CORRECTION

PATENT NO. : 5,162,733

DATED : November 10, 1992

INVENTOR(S) : Bernard A. Baldwin

It is certified that error appears in the above-identified patent and that said Letters Patent is hereby corrected as shown below:

In each of FIGS. 3, 4B, 5B, 6B, and 7B, the symbol "$2$" should read ---$l$---.

Column 4, line 42, the symbol "$l$" should read ---$T$---.

Signed and Sealed this

Twenty-eighth Day of December, 1993

Attest:

BRUCE LEHMAN

Attesting Officer       Commissioner of Patents and Trademarks